(12) United States Patent
Adami et al.

(10) Patent No.: US 7,351,860 B2
(45) Date of Patent: Apr. 1, 2008

(54) METHOD AND DEVICE FOR PRODUCING FORMIC ACID FORMATES AND USE OF SAID FORMATES

(75) Inventors: Christoph Adami, Weinheim (DE); Jörn Karl, Mannheim (DE); Alexander Hauk, Ludwigshafen (DE); Ralf Böhling, Griesheim (DE); Jörg Pastre, Bensheim (DE); Robert Lenz, Hochdorf-Assenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 268 days.

(21) Appl. No.: 10/524,268

(22) PCT Filed: Jul. 30, 2003

(86) PCT No.: PCT/EP03/08399

§ 371 (c)(1), (2), (4) Date: Feb. 11, 2005

(87) PCT Pub. No.: WO2004/020382

PCT Pub. Date: Mar. 11, 2004

(65) Prior Publication Data

US 2005/0245765 A1    Nov. 3, 2005

(30) Foreign Application Priority Data

Aug. 12, 2002 (DE) ............... 102 37 379

(51) Int. Cl.
*C07C 53/00* (2006.01)
(52) U.S. Cl. .................................... 562/609
(58) Field of Classification Search ............. None
See application file for complete search history.

(56) References Cited

U.S. PATENT DOCUMENTS

| | | |
|---|---|---|
| 2,545,889 A | 3/1951 | MacLean |
| 3,983,010 A | 9/1976 | Rauch et al. |
| 4,218,568 A | 8/1980 | Hohenschutz et al. |
| 4,261,755 A | 4/1981 | Berry et al. |
| 4,326,073 A | 4/1982 | Wolf et al. |
| 2003/0092939 A1 | 5/2003 | Strofer et al. |

FOREIGN PATENT DOCUMENTS

| | | |
|---|---|---|
| DE | 24 07 157 | 9/1975 |
| DE | 26 53 448 | 7/1977 |
| DE | 101 54 757 A1 | 5/2003 |
| DE | 102 10 730 A1 | 9/2003 |
| EP | 0 017 866 A1 | 10/1980 |
| WO | WO-96/35337 | 11/1996 |
| WO | WO-96/35657 | 11/1996 |
| WO | WO-97/05783 | 2/1997 |
| WO | WO-99/12435 | 3/1999 |
| WO | WO-00/08929 | 2/2000 |
| WO | WO-01/19207 | 3/2001 |

OTHER PUBLICATIONS

Bibliothek Gmelins Handbuch der anorganischen Chemie. Achte Vollig neu Bearbeitete Auflage. NATRIUM Mit 75 Figuren. System-Nummer 21. (1928) pp. 816-819.

Haupibucherei Gmelins Handbuch der anorganischen Chemie. 8. Auflage. Herausegeben von der Deutschen Chemischen Gesellschaft. System-Nummer 22: Kalium. Lieferung 3. Verbindungen bis Kalium und Tellur. (1937) pp. 919-921.

Deutsches Reich Reichspatentamt Patentschrift. Firma Rudolph Koepp & Co. in Oestrich i. Rhg. und Dr. Egon Elod in Karlsruhe i.B. Verfahren zur Herstellung saurer Natriumformiate. Patentiert im Deutschen Reiche vom. 27. Juni 1923 ab.

The Journal of the American Chemical Society. vol. XLIII Jul.-Dec. 1921 pp. 1470-1481. Compound Formation and Solubility in Systems of the Type, Formic Acid: Metal Formate (by James Kendall and Howard Adler Feb. 25, 1921).

Ullmann's Encyclopedia of Industrial Chemistry, Sixth Edition, 2000 Electronic Release Formic Acid—Production (Werner Reutemann, Heinz Kieczka).

*Primary Examiner*—Paul A. Zucker
(74) *Attorney, Agent, or Firm*—Connolly Bove Lodge and Hutz

(57) ABSTRACT

The invention relates to a method for producing formic acid formates, whereby (a) formic acid methyl ester is partially hydrolysed with water; (b) formic acid methyl ester and methanol are separated by distillation from the reaction mixture obtained in step (a), forming a current containing formic acid and water; (c) the current obtained in step (b), containing the formic acid methyl ester and optionally methanol, is converted into a current containing formate and water, by (i) reaction with a basic compound having a $pK_a$ value of the corresponding acid of the corresponding dissociation step of $=3$, measured at 25° C. in an aqueous solution, in presence of water, and (ii) separation by distillation of the methanol; and (d) the current obtained in step (b), containing formic acid and water, and the current obtained in step (c), containing formate and water, are combined to form a mixture containing the formic acid formate and water. The invention also relates to a device for producing said formic acid formates and to the use of the same.

13 Claims, 2 Drawing Sheets

METHOD AND DEVICE FOR PRODUCING FORMIC ACID FORMATES AND USE OF SAID FORMATES

CROSS REFERENCE TO RELATED APPLICATION

The present application is a National Stage application of PCT/EP2003/008399, filed Jul. 30, 2003, which claims priority from German Patent Application No. DE 102 37 379.5, filed Aug. 12, 2002.

In addition, the invention relates to the use of the acid formates for preserving and/or acidifying plant and/or animal materials, for treating biowastes and as an additive in animal nutrition and/or as growth promoters for animals.

Acid formates have an antimicrobial activity and are used, for example, for preserving and for acidifying plant and animal materials, for instance grasses, agricultural products or meat, for treating biowastes or as an additive for animal nutrition.

Acid formates and preparation methods for these have long been known. Thus, Gmelins Handbuch der anorganischen Chemie [Gmelin's Handbook of Inorganic Chemistry], 8$^{th}$ edition, Number 21, pages 816 to 819, Verlag Chemie GmbH, Berlin 1928 and Number 22, pages 919 to 921, Verlag Chemie GmbH, Berlin 1937 describes the synthesis of sodium diformate and of potassium diformate by dissolving sodium formate and potassium formate in formic acid. The crystalline diformates may be obtained by decreasing the temperature and by evaporating off excess formic acid.

DE 424 017 teaches preparing acid sodium formates having varying acid content by introducing sodium formate into aqueous formic acid in an appropriate molar ratio. By cooling the solution the corresponding crystals can be obtained.

According to J. Kendall et al., Journal of the American Chemical Society, Vol. 43, 1921, pages 1470 to 1481, acid potassium formates may be obtained by dissolving potassium carbonate in 90% strength formic acid, forming carbon dioxide. The corresponding solids can be obtained by crystallization.

U.S. Pat. No. 4,261,755 describes preparing acid formates by reacting an excess of formic acid with the hydroxide, carbonate or bicarbonate of the corresponding cation.

WO 96/35657 teaches preparing products which contain disalts of formic acid by mixing potassium formate, hydroxide, carbonate or bicarbonate, sodium formate, hydroxide, carbonate or bicarbonate, cesium formate, hydroxide, carbonate or bicarbonate or ammonium formate or ammonia with, possibly aqueous, formic acid, subsequently cooling the reaction mixture, filtering the resultant slurry and drying the resultant filter cake and recirculating the filtrate.

A disadvantage of the abovementioned processes is that, per mole of formate formed by the reaction with the basic compounds, in each case one mole of formic acid is consumed. This is because, as is known, it is precisely the preparation of concentrated, that is to say substantially anhydrous, formic acid, which is a process which requires extensive equipment, and is costly and energy-consuming. Thus the abovementioned processes, based on the entire value-added chain, require extensive equipment and are costly and energy-consuming.

German application No. 102 10 730.0 teaches preparing acid formates by reacting methyl formate with water and a basic compound having a pK$_a$ of the conjugate acid of the appropriate dissociation state of ≧3, and subsequently removing the methanol formed and optionally setting the desired acid content by adding formic acid.

German application No. 101 54 757.9 teaches preparing metal formate/formic acid mixtures by carbonylating the corresponding metal hydroxide to give the metal formate in the presence of water and a catalyst, removing the water and the catalyst by distillation and adding formic acid to the metal formate to produce the desired metal formate/formic acid mixture.

It is an object of the present invention, therefore, to provide a process which no longer has the abovementioned disadvantages, which makes it possible to prepare acid formates on an industrial scale in high yield and high space-time yield, with simultaneously high flexibility with respect to composition and with the use of readily accessible raw materials and which permits a simple process procedure with low capital costs and low energy consumption.

We have found that this object is achieved by a process for preparing acid formates, which comprises
(a) partially hydrolyzing methyl formates with water;
(b) separating off by distillation methyl formate and methanol from the reaction mixture obtained in process stage (a), forming a stream comprising formic acid and water;
(c) converting the stream comprising methyl formate with or without methanol from the process stage (b) by
  (i) reaction with a basic compound having a pK$_a$ of the conjugate acid of the appropriate dissociation state of ≧3, measured at 25° C. in aqueous solution, in the presence of water, and
  (ii) removal of the methanol by distillation, into a stream comprising formate and water; and
(d) combining the stream comprising formic acid and water from the process stage (b) and the stream comprising formate and water from the process stage (c), forming a mixture comprising the acid formate and water.

DETAILED DESCRIPTION OF EMBODIMENTS OF THE INVENTION

Figure 1:
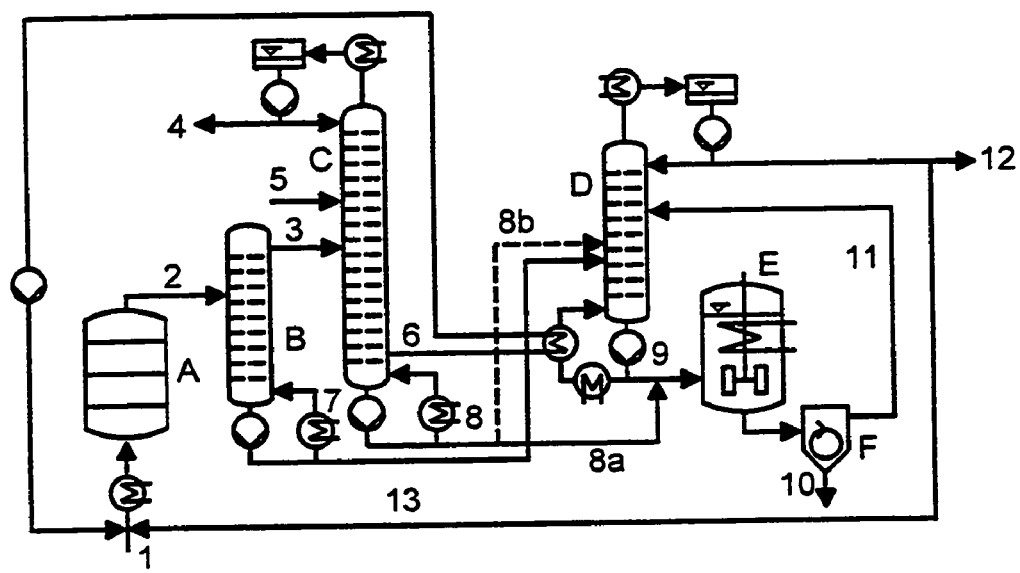
FIG. 1 shows a representative schematic of a process flow chart illustrating a first preferred embodiment of the invention.

Acid formates are compounds and mixtures which contain formate anions (HCOO$^-$), cations (M$^{x+}$) and formic acid (HCOOH). They can occur together in the form of a solid or a liquid and if appropriate contain other components, for example other salts, additives or solvents such as water. Generally, the acid formates can be represented by the formula $$HCOO^- M^{x+}_{1/x} * y\ HCOOH \qquad (I),$$

where M is a monovalent or polyvalent inorganic or organic cation, x is a positive integer and indicates the charge of the cation and y gives the molar fraction of formic acid based on the formate anion. The molar fraction of formic acid based on the formate anion y is generally from 0.01 to 100, preferably from 0.05 to 20, particularly preferably from 0.5 to 5, and in particular from 0.9 to 3.1.

The nature of the inorganic or organic cation M$^{x+}$ is in principle not critical, provided that this is stable under conditions under which the acid formate is to be handled. This also includes, for example, stability toward the reducing formate anion. Possible inorganic cations are the monovalent and/or polyvalent metal cations of metals of groups 1 to 14 of the Periodic Table of the Elements, for example lithium ($Li^+$), sodium ($Na^+$), potassium ($K^+$), cesium ($Cs^+$), magnesium ($Mg^{2+}$), calcium ($Ca^{2+}$), strontium ($Sr^{2+}$) and barium ($Ba^{2+}$), preferably sodium ($Na^+$), potassium ($K^+$), cesium ($Cs^+$) and calcium ($Ca^{2+}$). Possible organic cations are unsubstituted ammonium ($NH_4+$) and ammonium substituted by one or more carbon-containing radicals which may also be linked to one another, for example methylammonium, dimethylammonium, trimethylammonium, ethylammonium, diethylammonium, triethylammonium, pyrollidinium, N-methylpyrroldinium, piperidinium, N-methylpiperidinium or pyridinium.

A carbon-containing organic radical is an unsubstituted or substituted, aliphatic, aromatic or araliphatic radical having from 1 to 30 carbons. This radical can contain one or more heteroatoms, such as oxygen, nitrogen, sulfur or phosphorus, for example —O—, —S—, —NR—, —CO—, —N=, —PR— and/or —$PR_2$ and/or be substituted by one or more functional groups which, for example, contain oxygen, nitrogen, sulfur and/or halogen, for example by fluorine, chlorine, bromine, iodine and/or a cyano group (the radical R here is also a carbon-containing organic radical). The carbon-containing organic radical can be a monovalent or polyvalent radical, for example divalent or trivalent radical.

The individual process stages are described in more detail below:

Process Stage (a)

In process stage (a), methyl formate is partially hydrolyzed with water to formic acid and methanol. Partially means that only a portion of the methyl formate fed is hydrolyzed.

In the inventive process, in process stage (a) processes which are known per se for hydrolyzing methyl formate can be used. A general overview of known and industrially relevant processes for hydrolysis is given, for example, in Ullmann's Encyclopedia of Industrial Chemistry, 6$^{th}$ edition, 2000 electronic release, Chapter "FORMIC ACID, Production". Other suitable hydrolysis processes are also described, for example, in EP-A 0 005 998 and EP-A 0 017 866.

The hydrolysis is generally carried out at a temperature of from 80 to 150° C. and a pressure of from 0.5 to 2.0 MPa absolute. Reaction apparatuses which can be used are in principle all reaction apparatuses which are suitable for reactions in the liquid phase. Examples are stirred tanks and jet loop reactors. Preference is given to the use of a cascade reactor.

Generally, it is advantageous to carry out the hydrolysis in the presence of an acid catalyst, since this significantly increases the hydrolysis rate. Acid catalysts which can be used are the formic acid which is formed or additional catalysts. The additional catalysts can be of homogeneous or heterogeneous nature. Examples of heterogeneous catalysts are acid ion-exchangers, for example polysulfonic acids or poly(perfluoroalkylene)sulfonic acids (for example Nafion® from Du Pont) and examples of homogeneous catalysts are strong inorganic or organic acids, such as sulfuric acid, hydrochloric acid or alkyl- and tolylsulfonic acids. If homogeneous catalysts are used, these must generally be removed in a subsequent stage. Depending on the desired purity of the acid formates to be prepared, however, it is also possible to allow these to remain in the system. In this case, the acid catalysts are usually recovered in the form of their salts in the acid formate. Particularly preferably, the partial hydrolysis is carried out in the presence of formic acid as acid catalyst, which avoids adding an additional catalyst and its subsequent removal or possible contamination of the acid formates. Generally, for this purpose, at the reactor inlet a formic acid concentration of from about 0.1 to 2% by weight, based on the liquid mixture present which contains water and methyl formate, is established, by targeted addition of formic acid or a stream comprising formic acid.

The molar ratio of methyl formate to water to be used in the hydrolysis in the inventive process is generally from 0.1 to 10. Since this is an equilibrium reaction, an excess of water is preferably used, as also follows, for example, from the teaching of EP-A 0 017 866. Preferably in process stage (a), the methyl formate and the water are fed in a molar ratio of from 0.1 to 1, and particularly preferably from 0.15 to 0.3.

The reaction mixture obtained from the partial hydrolysis thus comprises unreacted methyl formate, formic acid, methanol and, owing to the preferred use of an excess of water, water.

Preferably, the aqueous reaction mixture comprises from 5 to 15 mol %, particularly preferably from 8 to 12 mol %, formic acid, from 3 to 10 mol %, particularly preferably from 6 to 12 mol %, methyl formate and from 6 to 15 mol %, particularly preferably from 8 to 12 mol %, methanol.

Process Stage (b)

In process stage (b), methyl formate and methanol are removed by distillation from the reaction mixture obtained in process stage (a), forming a stream comprising formic acid and water. Methyl formate and methanol can here in principle be removed together in the form of a stream or separately in the form of a stream comprising methyl formate and a stream comprising methanol. Generally, methyl formate and methanol are taken off separately or together in the upper part of the column. The stream comprising formic acid and water is generally taken off from the bottom. Preference is given in process stage (b) to the joint removal of a stream comprising methyl formate and methanol.

The design and operation of the distillation column is primarily dependent on the composition of the stream which is fed and on the desired purities of the two product streams and can be determined in a known way by those skilled in the art.

Process Stage (c)

In process stage (c), the stream comprising methyl formate with or without methanol from the process stage (b) is converted by (i) reaction with a basic compound having a $pK_a$ of the conjugate acid of the appropriate dissociation state of $\geq 3$, measured at 25° C. in aqueous solution, in the presence of water, and (ii) removal of the methanol by distillation into a stream comprising formate and water.

The basic compound to be used preferably has a $pK_a$ of the conjugate acid of the appropriate dissociation state of 23.5, particularly preferably $\geq 9$, and very particularly preferably $\geq 10$, measured at 25° C. in aqueous solution. The basic compound can be of inorganic or organic nature. The basic compound can be a salt or a covalent compound. The conjugate acid of the appropriate dissociation state is the acid formed by formal addition of a proton ($H^+$).

In the event that the basic compound is a salt, this can generally be represented by the formula $$M^{x+}{}_a A^{a-}{}_x \qquad (II),$$

where M and x have the meaning specified under (I) and A is an inorganic or organic anion having the charge "a–". The conjugate acid of the appropriate dissociation state is thus $HA^{(a-1)-}$. The appropriate dissociation equation defining the $pK_a$ to be considered is as follows $$HA^{(a-1)-} \rightleftharpoons A^{a-} + H^+ \quad (III).$$

In the event that the basic compound is a covalent compound B, the dissociation equation defining the $pK_a$ to be used is as follows $$HB^+ \rightleftharpoons B + H^+ \quad (IV).$$

Examples of suitable basic compounds are the salts $M^{x+}{}_a A^{a-}{}_x$ (II), where $M^{x+}$ is a monovalent or polyvalent metal cation of a metal as described above and $A^{a-}$ is an anion as listed in Table 1a and also the covalent compounds B as listed in Table 1b.

TABLE 1a

Possible anions $A^{a-}$ of suitable basic compounds and $pK_a$s (measured at 25° C. in aqueous solution) of the conjugate acids of the appropriate dissociation states.

| Anions $A^{a-}$ | Conjugate acid | $pK_a$ |
|---|---|---|
| Hydroxide (OH$^-$) | Water (H$_2$O) | 14.0 |
| Carbonate (CO$_3^{2-}$) | Hydrogen carbonate (HCO$_3^-$) | 10.3 |
| Hydrogen carbonate (HCO$_3^-$) | Carbonic acid (H$_2$CO$_3$) | 6.4 |
| Borate (BO$_3^{3-}$) | Hydrogen borate (HBO$_3^{2-}$) | >14 |
| Hydrogenborate (HBO$_3^{2-}$) | Dihydrogen borate (H$_2$BO$_3^-$) | >14 |
| Dihydrogenborate (H$_2$BO$_3^-$) | Boric acid (H$_3$BO$_3$) | 9.3 |
| Phosphate (PO$_4^{3-}$) | Hydrogen phosphate (HPO$_4^{2-}$) | 12.3 |
| Hydrogenphosphate (HPO$_4^{2-}$) | Dihydrogen phosphate (H$_2$PO$_4^-$) | 7.2 |
| Formate | Formic acid | 3.8 |
| Acetate | Acetic acid | 4.8 |
| Propionate | Propionic acid | 4.9 |
| Oxalate (C$_2$O$_4^{2-}$) | Hydrogen oxalate (HC$_2$O$_4^-$) | 4.2 |
| 2-Ethylhexanoate (C$_4$H$_9$—CH(C$_2$H$_5$)—COO$^-$) | 2-Ethylhexanoic acid (C$_4$H$_9$—CH(C$_2$H$_5$)—COOH) | >4 |

TABLE 1b

Possible covalent bases B as suitable basic compounds and $pK_a$s (measured at 25° C. in aqueous solution) of the conjugate acids of the appropriate dissociation states.

| Covalent base B | Conjugate acid | $pK_a$ |
|---|---|---|
| Ammonia | Ammonium | 9.3 |
| Methylamine | Methylammonium | 10.6 |
| Dimethylamine | Dimethylammonium | 10.7 |
| Trimethylamine | Trimethylammonium | 9.8 |
| Ethylamine | Ethylammonium | 10.7 |
| Diethylamine | Diethylammonium | 11.0 |
| Triethylamine | Triethylammonium | 10.8 |
| Pyrollidine | Pyrollidinium | 11.3 |
| N-Methylpyrrolidine | N-Methylpyrroldinium | 10.3 |
| Piperidine | Piperidinium | 11.1 |
| N-Methylpiperidine | N-Methylpiperidinium | 10.1 |
| Pyridine | Pyridinium | 5.3 |

Preferably, in the inventive process, the basic compound used is lithium hydroxide, lithium hydrogen carbonate, lithium carbonate, sodium hydroxide, sodium hydrogen carbonate, sodium carbonate, potassium hydroxide, potassium hydrogen carbonate, potassium carbonate, ammonium carbonate, ammonium hydrogen carbonate and/or ammonia, particularly preferably sodium hydroxide, sodium hydrogen carbonate, sodium carbonate, potassium hydroxide, potassium hydrogen carbonate, potassium carbonate and/or ammonia, and particularly preferably sodium hydroxide, sodium carbonate, potassium hydroxide and/or potassium carbonate, in particular sodium hydroxide and/or potassium hydroxide.

The manner in which the basic compounds are added is generally not important in the inventive process. They can be added in solid, liquid or gaseous form, as pure substance, as a mixture of substances or as solution. Examples are the addition in the form of aqueous solutions (for example aqueous solutions of the alkali metal salts or ammonia water), in the form of solid compounds (for example powders of the alkali metal salts), in the gaseous state (for example gaseous ammnonia). Preference is given to addition in the form of their aqueous solutions.

The order in which the starting materials are added is also generally not important in the inventive process. Thus it is possible, for example, to charge the basic compound in solid or liquid form (for example as aqueous solution) and then to introduce the stream comprising methyl formate in liquid or gaseous form. It is, in addition, possible to charge in liquid form the stream comprising methyl formate and then to add the basic compound. In addition, it is obviously also possible and, in particular when a continuous process is being carried out, advantageous, to combine the stream comprising methyl formate and the basic compound continuously.

The molar ratio of methyl formate to the basic compound is to be set advantageously in the inventive process stoichiometrically, that is to say in such a manner that the added methyl formate reacts with the added basic compound in accordance with the reaction stoichiometry to give the corresponding formate and water. The critical parameter for this is what is termed the molar equivalent of the basic compound, in which case here all dissociation states which lead by addition of protons to conjugate acids which have a $pK_a$ of $\geq 3$, measured at 25° C. in aqueous solution, must be taken into account. Thus, when potassium hydroxide is used as basic compound, preferably a molar ratio of methyl formate/potassium hydroxide of 1.0 is to be chosen, since this corresponds to the formation of potassium formate:

$$OH^- + H^+ \xrightleftharpoons[pK_a = 14]{} H_2O$$

When potassium carbonate is used as basic compound, preferably a molar ratio of methyl formate/potassium carbonate of 2.0 is to be chosen, since the conjugate carbonic acid is dibasic:

$$CO_3^{2-} + H^+ \xrightleftharpoons[pK_a = 10.3]{} HCO_3^-$$

$$HCO_3^- + H^+ \xrightleftharpoons[pK_a = 6.3]{} H_2CO_3$$

Deviations above and below the above stoichiometric addition are also possible in the inventive process, however. Thus, in the event of a deficit of basic compound there is the risk of incomplete reaction of the methyl formate and thus the risk of contamination of the methanol, which is to be removed by distillation, with unreacted methyl formate. In the event of an excess of basic compound, the resultant stream would, in addition to the corresponding formate and water, still contain the residual basic compound.

The amount of water to be used in the inventive process in the process stage (c) can vary over a broad range. Generally, from 20 to 90% by weight of water, and preferably from 40 to 50% by weight, based on the amount of methyl formate fed, is used in the reaction. Generally, the water is added via an aqueous solution of the basic compound, although it is also possible to add pure water.

The stream comprising methyl formate is generally reacted in process stage (c) with said basic compound in the presence of water at a temperature of from 0 to 150° C., preferably from 30 to 120° C., and particularly preferably from 50 to 80° C. During the procedure the pressure is generally from 0.05 to 1 MPa absolute, preferably from 0.08 to 0.5 MPa absolute and particularly preferably from 0.09 to 0.15 MPa absolute.

The reaction of the stream comprising methyl formate in process stage (c) with said basic compound in the presence of water is in principle independent of the removal of methanol by distillation.

The removal of methanol by distillation can therefore, in the inventive process, in principle take place before, during or after said reaction. Preferably, the methanol is removed by distillation together with, or after, said reaction.

When the methanol is removed by distillation before or after said reaction, in principle, all reaction apparatuses can be used for the reaction which are suitable for reactions in the liquid phase. Examples are stirred tanks and jet loop reactors. The methanol is removed by distillation here in a separate step, customarily in a distillation column.

In the inventive process, particular preference is given to removing the methanol by distillation together with reacting the methyl formate with the water and the basic compound, with conversion into the stream comprising formate and water in one column. On account of the lower boiling point of methyl formate compared with water, in this case the stream comprising methyl formate and methanol from the process stage (b) is advantageously added below the feed point of the water and the basic compound. Since the methyl formate and the methanol ascend in the column and the water and the basic compound flow downward, the column has a region suitable for said reaction. The methanol ascends and can be isolated overhead. Since methyl formate is generally prepared by carbonylating methanol, it is particularly advantageous to recirculate the methanol isolated overhead as feed stock for the preparation of methyl formate, the recirculating methanol in this variant by all means still being able to comprise residual amounts of methyl formate. Thus it is merely necessary in the overall balance to replace the small methanol losses by fresh methanol.

The stream comprising the aqueous formate flows downward in the column and is taken off as bottom stream. It can be advantageous here to withdraw a portion of the water as side stream at the bottom end of the column and to recirculate it to the hydrolysis. As a result of this measure, a more highly concentrated aqueous solution of the corresponding formate is also achieved.

The necessary residence time in the saponification part of the column can be provided, for example, by suitable internals, for example Thormann plates, or if appropriate by an external reaction volume. When an external reaction volume is provided, the stream to be saponified is withdrawn from the column at a suitable point via a side stream takeoff, fed to the external reaction apparatus and fed back to the column at a suitable point. In the context of the present invention, both variants are considered primarily equivalent.

The column is designed in a manner known and customary to those skilled in the art.

Process Stage (d)

In process stage (d), the stream comprising the formic acid and the water from process stage (b) and the stream comprising formate and water from process stage (c) are combined, forming a mixture comprising the acid formate and water.

The sequence of addition of the stream containing formic acid and the water from process stage (b) and the stream comprising the formate and water from process stage (c) is in general not critical in the inventive process. In particular, it is possible, and may be advantageous, to subject the stream comprising the formic acid and the water from process stage (b) and/or the stream comprising the formate and water from the process stage (c), before they are combined, to a concentration in formic acid or formate. In particular, the removal of a portion of the water present by evaporation, preferably by distillation, may be mentioned for this.

Temperature and pressure for the combining in process stage (d) are generally not critical. Generally, they are combined at a temperature of from 0 to 150° C. and a pressure of from 0.01 to 0.3 MPa absolute.

The apparatuses used can in principle be all apparatuses which are suitable for reactions in the liquid phase and, if appropriate, for reactions in the liquid phase with simultaneous removal of a volatile component. Examples are stirred tanks, jet loop reactors and columns. In addition, it is also possible to combine the two streams by their meeting within a pipe, advantageously having a downstream mixing section. In addition, it is also possible to combine the two streams in the apparatus in which solid acid formate is isolated.

The mixture obtained by combining the stream comprising the formic acid and the water from the process stage (b) and the stream comprising the formate and water from process stage (c) comprises the acid formate in the form of an aqueous solution, with or without previously precipitated acid formate as solid. Depending on requirements, in this form, it can be packaged, stored, transported and/or used for appropriate formulations or uses. In addition, the acid formate can be further concentrated or isolated as solid by downstream process steps.

Preference is given to a variant in which, in process stage (d),
(i) the stream comprising the formic acid and the water from the process stage (b), together with the mother liquor recirculated from step (iv), is concentrated in a column or an evaporator with removal of water by distillation;
(ii) the stream which was produced from step (i) by concentration and comprises formic acid, water and formate is combined with the stream comprising the formate and water from the process stage (c) forming a mixture comprising the acid formate and water;
(iii) solid acid formate from the mixture comprising acid formate and water obtained from step (ii) is precipitated by crystallization and this is isolated; and
(iv) the resultant mother liquor is recirculated to step (i).

The column or the evaporator in step (i) is generally to be operated in such a manner that a portion of the water fed can be taken off, for example overhead. The remaining stream comprising formic acid, water and formate generally has a water content of from 10 to 40% by weight and is withdrawn as bottom product. Said procedure has the advantage of a certain concentration of the stream comprising the formic acid and the formate. The water withdrawn from the column or the evaporator is advantageously recirculated to the hydrolysis stage in process step (a) and the excess is taken off from the process. The column or evaporator is designed in a manner known and customary to those skilled in the art.

The stream which is produced by concentration and comprises formic acid, water and formate can be combined with the stream comprising formate and water from process stage (c) forming a mixture comprising the acid formate and water in step (ii), for example, between the column and the crystallization apparatus, for example by combining two lines, or they can be combined in a separate mixing apparatus, or in the crystallization apparatus itself.

The crystallization procedure is generally known to those skilled in the art, with the precise design and procedure being able to take place in the customary manner. Generally, the crystallization is carried out at a temperature in the range from −20° C. to +80° C., and preferably from 0° C. to 60° C. Generally, the amount of product crystallized out increases with decreasing temperature. The crystallization can in principle be carried out in all known apparatuses for this. Said embodiment is particularly advantageously usable for removing acid formates which can crystallize in the desired composition. Relevant examples are potassium diformate (HCOOK.HCOOH), sodium diformate (HCOONa.HCOOH), sodium tetraformate (HCOONa.3 HCOOH) or mixtures thereof. The formates or acid formates which are crystallized out are generally removed by customary and known methods, for example by filtration or centrifugation.

The mother liquor which is produced in the crystallization of the solid acid formate is recirculated in step (iv) to step (i). Since this still comprises a considerable proportion of product of value, this thus also ensures its isolation. However, alternatively, it is also possible to use the value present in the mother liquor in a different manner, for example by direct use as solution.

Likewise, preference is given to a variant in which, in process stage (d)
(i) the stream from the process stage (b) comprising the formic acid and the water and the stream from the process stage (c) comprising the formate and the water are combined to form a mixture comprising the acid formate and water in a column or an evaporator with removal of water by distillation; and
(ii) solid acid formate is separated off by spray granulation, spray drying or melt crystallization from the mixture obtained from step (i) comprising acid formate and water, and this solid acid formate is isolated.

The two streams can be combined in step (i) upstream of the column or the evaporator, for example by joining two lines, or they can be combined in a separate mixing apparatus, or in the column or the evaporator, for example via two separate feeds.

The column or the evaporator in step (i) is generally to be operated in such a manner that a portion of the water fed can be taken off, for example overhead. The remaining acid-formate-containing mixture, which generally has a water content of from 0.5 to 30% by weight, is withdrawn as bottoms product. In particular in the isolation of the acid formate by means of melt crystallization, a lower water content generally from <1% by weight is set in the bottoms product. Said procedure has the advantage of a certain concentration of the stream comprising the acid formate. The water withdrawn from the column or the evaporator is advantageously recirculated to the hydrolysis stage in process step (a) and the excess taken off from the process. The column or the evaporator is designed in the manner known and customary to those skilled in the art.

The spray granulation, spray drying and melt crystallization procedures are generally known to those skilled in the art, in which case the precise design and procedure can be carried out in the customary manner. The abovementioned methods can also particularly advantageously be used for removing acid formates which can be crystallized in the desired composition. Relevant examples are potassium diformate (HCOOK*HCOOH), sodium diformate (HCOONa*HCOOH), sodium tetraformate (HCOONa*3 HCOOH) or mixtures thereof.

Since in the spray granulation, the spray drying and the melt crystallization, advantageously an aqueous acid formate having a low water content can be used, generally, also, only a small proportion of condensate or free amino acid is obtained.

Depending on the amount produced and the residual concentration of acid formate present, it may also be advantageous not to recirculate the stream, but to eject it from the system.

The inventive process can be carried out in principle batchwise, semicontinuously or continuously. Preferably, the inventive process is carried out continuously.

Preferably, in the inventive process, the acid formate prepared is acid metal formates, particularly preferably acid potassium formate, acid sodium formate, acid calcium formate or mixtures thereof and very particularly preferably potassium diformate (HCOOK.HCOOH), sodium diformate (HCOONa.HCOOH), sodium tetraformate (HCOONa.3 HCOOH) or mixtures thereof.

The acid formates are generally prepared in the form of their solutions, or crystalline as solids. If appropriate they can further be admixed with other components, for example other formate salts. In the case of the crystalline acid formates, it is generally advantageous for storage, transport and use, to compact these together with a dessicant, for example silicates or starch, to form a particulate compactate or diverse shaped bodies, for example tablets or beads.

In a particularly preferred embodiment, the simplified process flow chart which is shown in FIG. 1, via line (1), methyl formate and water comprising formic acid which is recirculated from the process are added to the cascade hydrolysis reactor (A). Generally, the two starting materials are brought to the desired inlet temperature in a heat exchanger premixed (as shown in the flow chart) or separately. The reaction mixture originating from the hydrolysis stage (process stage (a)), which reaction mixture comprises unreacted methyl formate, water, formic acid and methanol, is fed via line (2) to the column (B) in which the reaction mixture is separated by distillation into an overhead stream comprising methyl formate and methanol, and a bottoms stream comprising aqueous formic acid (process stage (b)). The overhead stream comprising methyl formate and methanol is fed via line (3) to column (C). In addition, the aqueous basic compound, particularly preferably potassium hydroxide solution, is fed to the column (C) above the inlet point of the stream comprising methyl formate and methanol via line (5). Methanol is recovered overhead from column (C) and is preferably recirculated for repeated preparation of methyl formate by carbonylation. At the bottom end of column (C), a portion of the water is withdrawn and recirculated via line (6) to the hydrolysis stage. The bottoms product obtained is an aqueous potassium formate solution. The stream comprising aqueous formic acid from process stage (b) is fed via line (7) to the column (D). If appropriate, a portion of the stream comprising the aqueous formate solution from process stage (c) is also fed via lines (8) and (8*b*). The column (D) is advantageously operated in such a manner that the bottoms product obtained is a concentrated mixture comprising formic acid, formate and water having a water content of generally from 10 to 40% by weight. A portion of the water is withdrawn from the column (D) in the form of a formic-acid-containing water stream as overhead product and recirculated via line (13) to the hydrolysis stage. A portion of the water stream comprising small amounts of formic acid can here optionally be withdrawn from the system via line (12). The bottoms product of column (D) is fed via line (9) to an apparatus (E) suitable for crystallization, for example a cooling disc crystallizer. The stream comprising the aqueous formate solution is fed from the process stage (C) via line (8a). The feed in this case can be performed, for example, by combining two lines (as shown in FIG. 1) or directly into the crystallization apparatus. The crystallization is primarily performed by temperature decrease. The resultant crystals are fed together with the supernatant solution for separation to the apparatus (F). Preferably the separation is performed by centrifugation. The separated crystals are withdrawn via line (10) and can be dried and/or compounded, for example in optional following stages. The resultant mother liquor is recirculated via line (11) to the column (D).

Figure 2:
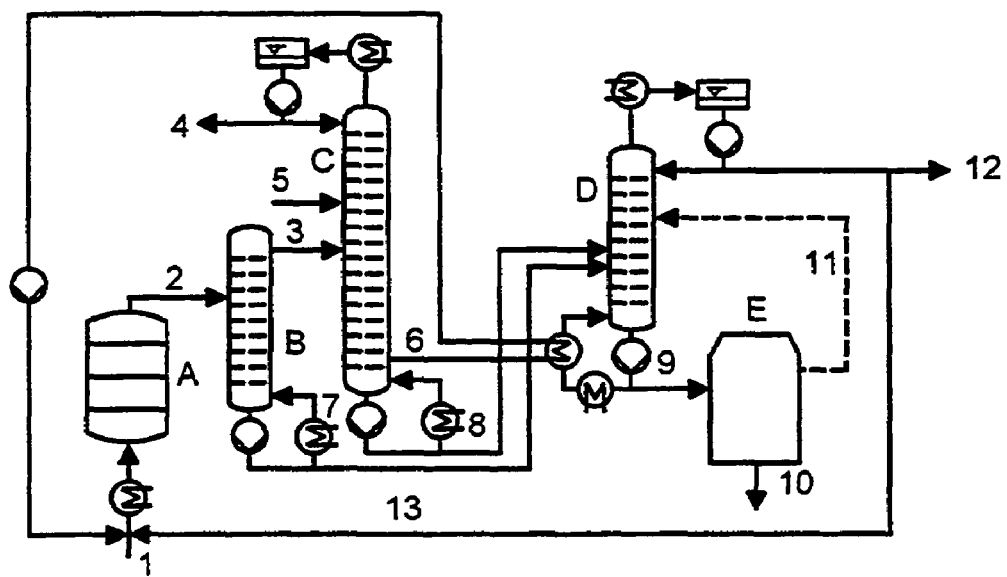
FIG. 2 shows a representative schematic of a process flow chart illustrating a second preferred embodiment of the invention.

In another particularly preferred embodiment, whose simplified process flow chart is shown in FIG. 2, the process stages (a), (b) and (c) are carried out as described in the above particularly preferred embodiment. The stream comprising the aqueous formic acid from the process stage (b) is fed via line (7) and the stream comprising the aqueous formate solution from the process stage (c) is fed via line (8) to the column (D). The column (D) is advantageously operated in such a manner that the bottom product obtained is a concentrated mixture comprising formic acid, formate and water having a water content generally from 0.5 to 30% by weight. A portion of the water fed is withdrawn from the column (D) as overhead product in the form of a formic-acid-containing water stream and is recirculated via line (13) to the hydrolysis stage. A portion of the water stream comprising small amounts of formic acid can here optionally be withdrawn from the system via line (12). The bottoms product of the column (D) is fed via line (9) to an apparatus (E) suitable for spray granulation, spray drying or melt crystallization. The resultant solid acid formate is withdrawn via line (10) and can be dried and/or compounded, for example in optional following stages. The resultant condensate can optionally be recirculated via line (11) to the column (D) or ejected from the system.

The inventive process makes it possible to prepare acid formates on an industrial scale in high yield and high space-time yield, with simultaneously high flexibility with respect to composition and using readily accessible raw materials with simple process design and low capital costs. In addition, the process has the critical advantage that not only the formate, but also the formic acid, can be produced directly from the methyl formate without the costly diversion, which is expensive in terms of resources, via the concentrated formic acid. The inventive process is therefore simple to carry out in processing terms and compared with the processes involving direct use of concentrated formic acid according to the prior art, has markedly lower capital costs and a markedly lower energy consumption. In addition, in part the use of high-alloy steels can be avoided, since the acid formates are much less corrosive than concentrated formic acid.

In addition, the invention relates to an apparatus for preparing the acid formates according to the inventive process, comprising (a) a reactor (A) suitable for hydrolyzing methyl formate;
(b) a column (B) suitable for separating by distillation a stream comprising methyl formate, formic acid, methanol and water into methyl formate, methanol and a stream comprising formic acid and water, which column is connected on the feed side to the reactor (A);
(c) a column (C) suitable for saponifying methyl formate with a basic compound and for removing methanol by distillation, which column is connected on the feed side to the column top of column (B) and has above said feed an inlet point for the basic compound; and
(d) a column (D) suitable for removing water from a stream comprising formic acid and water, which column is connected on the feed side to the column bottom of column (B).

A suitable reactor (A) is, for example, a stirred tank or a jet loop reactor. Preference is given to a cascade reactor. The reactor (A) is designed according to the manner customary and known to those skilled in the art.

The column (B) is designed in the manner which is customary and known to those skilled in the art.

The column (C) can comprise suitable internals in the saponification part for providing the residence time required for the process, for instance Thormann plates, or if appropriate an external reaction volume connected to the column. The external reaction volume which may be present is generally connected to the column via a suitable side stream takeoff and a suitable side stream feed. The column (C) is designed in the manner which is customary and known to those skilled in the art.

The column (D) is designed in the manner customary and known to those skilled in the art.

A preferred apparatus is an apparatus which, in addition to the abovementioned features (a) to (d), comprises (e) an apparatus (E) suitable for crystallizing acid formate, which apparatus is connected on the feed side to the column bottom of column (D) and to the column bottom of column (C);
(f) an apparatus (F) suitable for separating off crystals of the acid formate, which apparatus is connected on the feed side to apparatus (E); and
(g) a connection line (11) between apparatus (F) and column (D), which connection line is suitable for recirculating mother liquor.

The apparatuses (E) and (F) are designed in the manner which is customary and known to those skilled in the art.

Furthermore, the preferred apparatus is an apparatus which, in addition to the abovementioned features (a) to (d), comprises (e) a connection line (8) between the column bottom of column (C) and column (D), which connection line is suitable for feeding aqueous formate; and
(f) an apparatus (E) suitable for spray granulation, spray drying or melt crystallization, which apparatus is connected on the feed side to the column bottom of column (D).

The apparatus (E) is designed in the manner which is customary and known to those skilled in the art.

In addition, the invention relates to the use of the inventively prepared acid formates for preserving and/or acidifying plant and animal materials. Examples are the use of acid formates for preserving and acidifying grass, agricultural plants, fish and fish products and meat products, as are described, for example, in WO 97/05783, WO 99/12435, WO 00/08929 and WO 01/19207.

Furthermore, the invention relates to the use of the inventively prepared acid formates for treating biowastes. The use of acid formates for treating biowastes is described, for example, in WO 98/20911.

In addition, the invention relates to the use of the inventively prepared acid formates as additive in animal nutrition and/or as growth promoters for animals, for example for breeding sows, growing/finishing pigs, poultry, calves, cows and fish. Said use is described, for example, in WO 96/35337. Preference is given to the use of the inventively prepared acid potassium formates, in particular potassium diformate, as additive in animal nutrition and/or as growth promoters for animals, in particular for breeding sows and growing/finishing pigs.

Very particularly preferred mixtures for the preferred use of the acid potassium formates prepared by the inventive process as additive in animal nutrition and/or as growth promoters for animals are the following two compositions:

|  | Mixture 1 (% by weight) | Mixture 2 (% by weight) |
| --- | --- | --- |
| Potassium diformate | 20 to 60 | 60 to 99 |
| Sodium diformate/tetraformate | 20 to 50 | — |
| Calcium formate | 0 to 25 | 0 to 28 |
| Dessicant (silicate or starch) | 0 to 4 | 0 to 4 |
| Water | 0 to 5 | 0 to 5 |

Very particular preference is given to the use of the inventively prepared potassium diformate as additive in animal nutrition and/or as growth promoter for animals in the form of a product of composition 98.0±1% by weight potassium diformate, 1.5±1% by weight silicate and 0.5±0.3% by weight water.

We claim:

1. A process for preparing acid formates comprising:
   (a) partially hydrolyzing methyl formates with water;
   (b) separating off by distillation methyl formate and methanol from the reaction mixture obtained in process stage (a), forming a stream comprising formic acid and water;
   (c) converting the stream comprising methyl formate with or without methanol from the process stage (b) by
      (i) reaction with a basic compound having a $pK_a$ of the conjugate acid of the appropriate dissociation state of $\geq 3$, measured at 25° C. in aqueous solution, in the presence of water, and
      (ii) removal of the methanol by distillation, into a stream comprising formate and water; and
   (d) combining the stream comprising formic acid and water from the process stage (b) and the stream comprising formate and water from the process stage (c), forming a mixture comprising the acid formate and water.

2. The process according to claim 1, wherein, in the process stage (a), the methyl formate and the water are fed in a molar ratio of 0.1 to 1.

3. The process according to claim 1, wherein, in the process stage (c), the removal of the methanol by distillation and the reaction of the methyl formate with the water and basic compound with transfer into the stream comprising formate and water are carried out together in one column.

4. The process according to claim 1, wherein, in process stage (d):
   (i) the stream comprising the formic acid and the water from the process stage (b), together with the mother liquor recirculated from step (iv), is concentrated in a column or an evaporator with removal of water by distillation;
   (ii) the stream which was produced from step (i) by concentration and comprises formic acid, water and formate is combined with the stream comprising the formate and water from the process stage (c) forming a mixture comprising the acid formate and water;
   (iii) solid acid formate from the mixture comprising acid formate and water obtained from step (ii) is precipitated by crystallization and this is isolated; and
   (iv) the resultant mother liquor is recirculated to step (i).

5. The process according to claim 1, wherein, in process stage (d):
   (i) the stream from the process stage (b) comprising the formic acid and the water and the stream from the process stage (c) comprising the formate and the water are combined to form a mixture comprising the acid formate and water in a column or an evaporator with removal of water by distillation; and
   (ii) solid acid formate is separated off by spray granulation, spray drying or melt crystallization from the mixture obtained from step (i) comprising acid formate and water, and this solid acid formate is isolated.

6. The process according to claim 1, wherein, in process step (c), the basic compound is selected from the group consisting of sodium hydroxide, sodium hydrogen carbonate, sodium carbonate, potassium hydroxide, potassium hydrogen carbonate, potassium carbonate and ammonia.

7. The process according to claim 1, wherein the acid formate prepared is selected from the group consisting of acid potassium formate, acid sodium formate, acid calcium formate and mixtures thereof.

8. The process according to claim 1, wherein the acid formate prepared is selected from the group consisting of potassium diformate, sodium diformate, sodium tetraformate and mixtures thereof.

9. The process according to claim 2, wherein, in the process stage (c), the removal of the methanol by distillation and the reaction of the methyl formate with the water and basic compound with transfer into the stream comprising formate and water are carried out together in one column.

10. The process according to claim 2, wherein, in the process stage (d):
    (i) the stream comprising the formic acid and the water from the process stage (b), together with the mother liquor recirculated from step (iv), is concentrated in a column or an evaporator with removal of water by distillation;
    (ii) the stream which was produced from step (i) by concentration and comprises formic acid, water and formate is combined with the stream comprising the formate and water from the process stage (c) forming a mixture comprising the acid formate and water;
    (iii) solid acid formate from the mixture comprising acid formate and water obtained from step (ii) is precipitated by crystallization and this is isolated; and
    (iv) the resultant mother liquor is recirculated to step (i).

11. The process according to claim 3, wherein, in the process stage (d):
    (i) the stream comprising the formic acid and the water from the process stage (b), together with the mother liquor recirculated from step (iv), is concentrated in a column or an evaporator with removal of water by distillation;
    (ii) the stream which was produced from step (i) by concentration and comprises formic acid, water and formate is combined with the stream comprising the formate and water from the process stage (c) forming a mixture comprising the acid formate and water;

(iii) solid acid formate from the mixture comprising acid formate and water obtained from step (ii) is precipitated by crystallization and this is isolated; and (iv) the resultant mother liquor is recirculated to step (i).

12. The process according to claim 2, wherein, in process stage (d):

(i) the stream from the process stage (b) comprising the formic acid and the water and the stream from the process stage (c) comprising the formate and the water are combined to form a mixture comprising the acid formate and water in a column or an evaporator with removal of water by distillation; and (ii) solid acid formate is separated off by spray granulation, spray drying or melt crystallization from the mixture obtained from step (i) comprising acid formate and water, and this solid acid formate is isolated.

13. The process according to claim 3, wherein, in process stage (d):

(i) the stream from the process stage (b) comprising the formic acid and the water and the stream from the process stage (c) comprising the formate and the water are combined to form a mixture comprising the acid formate and water in a column or an evaporator with removal of water by distillation; and (ii) solid acid formate is separated off by spray granulation, spray drying or melt crystallization from the mixture obtained from step (i) comprising acid formate and water, and this solid acid formate is isolated.

* * * * *